United States Patent
Bhatt et al.

(10) Patent No.: US 6,274,129 B1
(45) Date of Patent: Aug. 14, 2001

(54) HAIR STYLING GELS

(75) Inventors: Darshna Bhatt, Schaumburg; Riaz Rizvi; Ramiro Galleguillos, both of Glendale Heights, all of IL (US)

(73) Assignee: Helene Curtis, Inc., Chicago, IL (US)

(*) Notice: Subject to any disclaimer, the term of this patent is extended or adjusted under 35 U.S.C. 154(b) by 0 days.

(21) Appl. No.: 09/596,997

(22) Filed: Jun. 20, 2000

Related U.S. Application Data

(62) Division of application No. 08/717,429, filed on Sep. 20, 1996, now Pat. No. 6,132,704.

(51) Int. Cl.$^7$ .................................................. A61K 7/11
(52) U.S. Cl. .................................. 424/70.11; 424/DIG. 2
(58) Field of Search ................................ 424/70.1, 70.11, 424/401, 63, 70.15, DIG. 1, DIG. 2

(56) References Cited

U.S. PATENT DOCUMENTS 6,132,704 * 10/2000 Bhatt et al. .

* cited by examiner

*Primary Examiner*—Edward J. Webman
(74) *Attorney, Agent, or Firm*—Matthew Boxer

(57) ABSTRACT

Hair styling gels containing a carboxylated polyurethane resin, a viscosity enhancer, and an optional second hair fixative resin, in an aqueous carrier, are disclosed. The styling gel compositions impart excellent hair styling, conditioning, and hair set retention properties to treated hair.

2 Claims, No Drawings

HAIR STYLING GELS

This application is a Divisional of Ser. No. 08/717,429 filed Sep. 20, 1996, U.S. Pat. No. 6,132,704.

FIELD OF INVENTION

The present invention is directed to hair styling gels that are applied to the hair to shape, style, and condition the hair. The gels have excellent hair styling, detangling, and style retention properties, and are washable from treated hair. In particular, the present invention relates to hair styling gels comprising a carboxylated polyurethane resin, an optional second hair fixative resin, a viscosity enhancer, and a carrier comprising water.

BACKGROUND OF THE INVENTION

Normal hair can be so fine, limp, and lacking in body that the hair does not hold a hair set well. Furthermore, hair can lose body and be weakened as a result of being subjected to chemically active hair treatments, such as permanent waves and tints. Additionally, hair can be weakened even further by other contributing factors, such as bleaching by the sun or chlorinated swimming pool water.

The condition and appearance of hair can be improved by applying a composition that conditions the hair and helps maintain the hair in a predetermined configuration, or hairstyle. Hair setting and conditioning can be achieved by applying such a composition to wet hair, fixing the hair by drying, then combing to give finishing touches and provide the desired hairstyle. Similarly, after applying the composition to the hair, the wet hair can be set by using any of a variety of rollers or curlers to mechanically fix the hair in a predetermined configuration before drying. In either case, the wet hair is dried, either by ambient air drying, electric drying, or hot air, i.e., blow, drying, to set the hair.

The inherent problem encountered in hair setting is the natural tendency of hair to return to its natural shape. For example, set hair returns to its natural shape almost immediately if moistened. Likewise, high humidity conditions accelerate the tendency of hair to return to its natural shape. Therefore, intensive efforts have been directed toward providing a hair set with sufficient holding power to maintain the desired hairstyle until at least the next shampoo, and, accordingly, giving the hair set a degree of permanency.

As indicated by the natural tendency of hair to return to its natural shape, hair is an elastic structure. As a result, the slight deformations in hair structure resulting from setting the hair are completely reversible. However, the rate of return of hair to its natural shape is dependent upon the method used to deform, or set, the hair. Hair sets performed with wet strands of hair being rolled tightly, either in curls around the finger or on curlers, followed by drying the hair and unrolling the curlers after drying, corresponds to the release of the hair from a deformation-causing load. The deformation, or set, obtained can last for several days, but the hair set is not retained if the hair is wetted.

Investigators have sought to delay the combined action of natural forces and moisture that cause hair to return to its original state by applying compositions containing naturally occurring or synthetic polymers that assist the hair in retaining the desired hairstyle configuration. When applied to hair from aqueous or aqueous/alcoholic solutions, gels, or mousses, the polymers form a film on the hair, after drying, to help maintain the hair in the desired hair set configuration. The polymeric film promotes cohesion and gives stability to the hair set, and also acts as a moisture barrier. The principal objective of a hair styling composition, therefore, is to cover the styled hair with an invisible polymeric film that gives the styled hair a degree of rigidity, protects the hairstyle against wind and humidity, retains the hairstyle, and imparts a good feel and conditioning to the styled hair.

One type of hair styling composition is a hair spray product. Hair spray products are applied to wet and/or dry hair and contain a polymer, or polymer mixture, that remains fixed on the previously styled hair and effects the hair in various ways. For example, a "mechanical" effect is exerted on each individual hair. The film-forming polymers are used to provide a flexible sheath of polymeric film on the shaped hair after drying, and, therefore, for mechanical reasons, retard the return of each individual hair to its natural shape. In addition, the polymeric film provides an overall stiffening of the hair. The hair behaves as if the individual hair strands are welded together, and the final hairstyle has better cohesion, therefore, resisting the natural forces that return the hair to its natural shape. Finally, the polymeric film protects the hair from humidity. The ability of the polymeric film to attract and absorb water preferably is minimal, such that the polymeric film retards moisture uptake by hair and retards the return of the hair to its natural state.

Hair styling gels are another type of hair styling composition. Hair styling gels are applied to wet or damp hair prior to configuring the hair in a predetermined configuration. Hair styling gels are applied by rubbing the gel onto the hair manually. The treated hair then is dried and set in a desired configuration, such as with a blow dryer.

The general principles of hair styling and setting are thoroughly discussed by C. Zviak, in *The Science of Hair Care*, Marcel Dekker, pp. 149–181 (1986). Zviak reviews both the polymers used in hair styling products and the formulation principles used to produce a hair styling composition that provides such beneficial hair set properties as improved hairstyle retention, easy application and combing, quick drying and nonstickiness, good hair body and bounce, increased hair volume and gloss, and hydrophobicity. It is evident that in the formulation of any end-use hair styling product, some of these benefits must be sacrificed to some degree to achieve a competing benefit. Therefore, the formulation of hair styling compositions has proved difficult.

To overcome some of the inherent disadvantages of the polymers used to set and style hair, and to minimize the drawbacks of a particular polymer used in the formulation, hair styling compositions are available in diversified forms. For example, hair styling compositions are available as plasticizing lotions, plasticizing gels, aerosol foams, all-purpose lotions, hair sprays, holding lotions, conditioners, and shampoos.

Nonionic, cationic, and anionic polymers have been used in hair styling compositions, with the anionic polymers providing the best hair set results. However, anionic polymers also have disadvantages, such as high water solubility, and, therefore, low hydrophobicity; and low substantivity on hair fibers, therefore, generating a crust and flaking due to easy elimination from the hair by combing and brushing. As a result, investigators have continued to search for compounds and compositions that provide the benefits of improved durability and feel of the hair set, while conditioning the hair.

The use of resins, or polymers, in hair styling compositions is well known, as summarized in Grollier et al. U.S. Pat. No. 4,445,521. The resins typically used in hair styling compositions are linear vinyl (e.g., an alkyl vinyl ether) or acrylic (e.g., an alkyl acrylate) polymers prepared by copolymerizing two or more monomers in a free radical polymerization reaction. The vinyl and acrylic-based resins often are used in relatively high concentrations in a hair styling composition to fix the hair in a particular configuration and to provide good hair set retention. However, at high concentrations, the vinyl and acrylic-based resins exhibit disadvantages that adversely affect the hair, such poor combing, poor feel, and excessive stiffness, crust, and flaking.

The vinyl and acrylic-based hair fixative resins conventionally used in hair styling compositions were designed for use in anhydrous alcoholic hair spray compositions. The resins, therefore, had excellent compatibility with, and solubility in, alcohols (e.g., ethanol) used in pump spray compositions and hydrocarbons used as propellants in aerosol compositions. However, due to environmental and toxicological concerns, government regulations require a decrease in the amount of organic solvents used in hair setting and related compositions. Therefore, the alcohols and the hydrocarbon gases traditionally present in hair setting compositions, and especially hair sprays, are being replaced with water and water-soluble solvents, like dimethyl ether, that pose less harm to the environment. In addition, the traditional hair sprays are being replaced by hair styling gels and mousses.

The solvent changes required by government regulation made the traditional vinyl and acrylic-based resins unsuitable in aqueous hair setting compositions. The presence of water in hair spray compositions increased the viscosity of the composition, thereby making spraying difficult to impossible when traditional resins are used. The relatively high viscosity of the hair spray compositions, therefore, required a reduction in the resin concentration of the composition, which, in turn, results in insufficient hair set retention. The presence of water also increases the tackiness of the resin on the hair, thereby prolonging the drying time of the hair spray on the hair. Water also reduces the hair-wetting ability of the compositions, resulting in beading and flaking of the resin from the hair. In the case of aerosol hair spray products, the combination of water, resin, and propellant gas results in poor delivery and foaming of the composition, large aerosol particle size, and beading of the resin. Similar disadvantages were observed when a traditional hair fixative resin was used in an aqueous hair styling gel.

The disadvantages attributed to traditional vinyl and acrylic resins led investigators to search for new hair fixative resins that overcome the disadvantages associated with the vinyl and acrylic resins. As set forth in European Patent Application 0 619 111, one class of resins is the polyurethanes. However, the hair fixative compositions disclosed in EP 0 619 111 require a base to neutralize, and solubilize, the polyurethane resin. It would be desirable to provide an aqueous hair styling gel that overcomes the disadvantages associated with traditional vinyl and acrylic resins, that imparts good hair style and a natural feel to the hair, that retains the hair set, and that conditions the hair.

SUMMARY OF THE INVENTION

The present invention is directed to hair styling gels containing (a) a hydrophilic, carboxylated polyurethane resin, (b) an optional second hair fixative resin, (c) a viscosity enhancer, and (d) a carrier comprising water. The optional second hair fixative resin is a traditional hair setting resin, such as a vinyl or acrylic resin. The optional second hair fixative resin can be an anionic, cationic, or nonionic resin because each class of resin is compatible with the carboxylated polyurethane resin.

The hair styling gels impart good hair set retention and a soft, natural feel to treated hair, and provide superior hairstyle retention at high relative humidity. The hair styling gels also detangle hair and condition the hair. Such results are unexpected because traditional hair setting resins are hydrophobic. In contrast, the carboxylated polyurethane resins are hydrophilic, yet provide a soft, natural feel to the hair, and the hair is not tacky.

In particular, the present invention is directed to hair styling gels comprising: (a) about 0.25% to about 6%, by total weight of the composition, of a carboxylated polyurethane resin, (b) 0% to about 6%, by total weight of the total composition, of an optional second hair fixative resin, (c) about 0.01% to about 3%, by total weight of the composition, of a viscosity enhancer, (d) 0% to about 20%, by total weight of the composition, of an alcohol, like ethanol, and (e) water. The hair styling gels have a pH of about 6 to about 10, and a viscosity of about 10,000 to about 100,000 cps (centipoise). In a preferred embodiment, the weight ratio of the second hair fixative resin to the carboxylated polyurethane resin is 0 to about 1.

The polyurethane resins used in the hair styling gels, also termed a polycarbamyl polyglycols, have pendant carboxyl groups and are hydrophilic. The carboxyl groups can be a carboxylic acid group (i.e., $CO_2H$), an ester group (i.e., $CO_2R$, wherein R is an alkyl group containing one to three carbon atoms), or a mixture thereof. The polyurethane resin also can be a copolymer of polyvinylpyrrolidone and a polyurethane, termed a PVP/polycarbamyl polyglycol ester.

The polyurethane resins have good tear strength, excellent washability, good adhesion, and are soluble in water and polar solvents, thereby making them useful in aqueous hair styling compositions. In addition, the polyurethane resins, alone and in combination with the optional second hair fixative resin, form clear, i.e., transparent, compositions in neutral to slightly basic aqueous solvents. The carboxylated polyurethane resins form flexible, elastic films that give treated hair a natural feel, while retaining the desired hairstyle.

The hair styling gels can be designed to impart a natural feel, a conditioned feel, or a stiff feel to treated hair by incorporating an optional second hair fixative resin in the gel, and by a judicious selection of the second hair fixative resin and of the amount of the second hair fixative resin in the hair styling gel. The hair styling gels provide a soft polymeric film on the hair after application because of the associative nature of the carboxylated polyurethane resin. The optional second hair fixative resin is included in the hair styling gel to impart a desired degree of stiffness to treated hair. The hair styling gels, therefore, impart superior hair set retention, good conditioning properties, and can be designed to impart any desired feel to treated hair.

In accordance with another important aspect of the present invention, the hair styling gels exhibit improved washability from the hair when the carboxylated polyurethane resin has an acid value of at least about 7 mg KOH/g (milligrams potassium hydroxide per gram of resin), and preferably about 7 to about 50 mg KOH/g of resin. The carboxylated polyurethane resins do not require neutralization with a base to provide a useful hair styling gel.

In accordance with one embodiment of the present invention, the carboxylated polyurethane resin is a copolymer of polyvinylpyrrolidone and a polyurethane. In another embodiment, the carboxylated polyurethane resin used in the hair styling gel is produced by reacting: (a) a diol component comprising a polyoxyalkylene diol; (b) an alkylene glycol; (c) a diisocyanate; (d) water in an amount of about 0.01% to about 0.45% by weight of the mixture; and (e) a 2,2-di(hydroxymethyl)alkanoic acid, preferably 2,2-di-(hydroxymethyl)propionic acid, wherein the ratio of NCO (isocyanate) groups to OH (hydroxyl) groups in the water, diol, and glycol, i.e., the R-value, is about 0.5 to about 1.

The hydrophilic, carboxylated polyurethane resin contains polyoxyalkylene units, i.e., soft segments, and/or alkylene units, i.e., hard segments, connected by urethane linkages. Preferably, the carboxylated polyurethane resin contains soft and hard segments. Also incorporated into the polymer chain is a small amount of diol having a pendant carboxyl group. The polymer chain further contains urea linkages resulting from a reaction between water and isocyanate groups, which modify the hair styling properties of the polyurethane.

Polyoxyethylene soft segments of the polyurethane resin impart hydrophilicity to the polyurethane. Soft segments derived from polyoxypropylene and polyoxytetramethylene diols provide a softer, but less hydrophilic, polyurethane. Hydrophilic polyurethane resins having improved strength and superior adhesive properties can be formed by using combinations of polyoxyalkylene diols.

In another embodiment of the present invention, the carboxylated polyurethane resins used in the hair spray composition are produced from (a) a major portion of polyoxyethylene diol having a number average molecular weight ($M_n$) of 6000 to 10,000; (b) an alkylene glycol, preferably diethylene glycol, cyclohexanedimethanol, or dipropylene glycol; (c) a diisocyanate; (d) water in the amount of about 0.01% to about 0.45% by weight; and (e) a 2,2-di-(hydroxymethyl)alkanoic acid, wherein the ratio of NCO to OH in the water, diol, and glycol mixture (i.e., the R-value) is about 0.6 to about 0.98. These polyurethane resins are soluble in dilute (neutral to basic) aqueous solutions, and exhibit good sprayability, superior feel, low flaking, desirable crust, and good set retention when applied to hair. The polyurethane resins are hydrophilic, and provide a soft feel in a hydrated state. In a particular embodiment of a polyurethane resin produced with a major portion of polyoxyethylene diol, water is added in the amount of about 0.04% to about 0.25% by weight, and the ratio of NCO to OH of the water, diol and glycol mixture (i.e., the R-value) is about 0.6 to about 0.98 to provide a carboxylated polyurethane resin having improved adhesiveness to the hair and improved slip, i.e., good combing properties.

Another aspect of the present invention is to provide a hair styling gel that provides good hair set retention at high relative humidity, imparts a soft, natural, nontacky feel to the hair, and conditions and detangles the hair. Accordingly, a hydrophilic polyurethane resin incorporated into a present hair spray composition has a weight average molecular weight of about ($M_w$) of about 15,000 to about 300,000, preferably 30,000 to about 200,000, and to achieve the full advantage of the present invention about 40,000 to about 190,000. The polyurethane resins also have a polydispersibility index (PDI) of about 1 to about 4, and preferably about 1 to about 3. Preferred polyurethane resins have an R-value of about 0.65 to about 0.98.

In accordance with another important aspect of the present invention, the carboxylated polyurethane resin modifies the properties of the optional second hair setting resin to provide a clear, i.e., transparent, hair styling gel that can be easily applied to the hair to give the hair a natural through a stiff feel, as desired, while conditioning the hair and imparting good set retention without excessive crust formation or flaking.

DETAILED DESCRIPTION OF THE INVENTION

The present hair styling gels contain a carboxylated polyurethane resin, an optional second hair setting resin, and a viscosity enhancer in an aqueous carrier. The polyurethane resins are soluble in water and in a broad range of water/alcohol mixtures, and help solubilize the second hair fixative resin to provide a clear composition. The carboxylated polyurethane resins also possess thermal properties that allow styling of the hair with curling irons and blow dryers. The present hair styling gels, therefore, overcome problems and disadvantages associated with compositions which contain only a traditional acrylic or vinyl-based hair fixative resin, and provide improved hair styling, hair set retention, hair feel and conditioning, and washability.

In particular, the present hair styling gels comprise about 0.25% to about 6%, and preferably about 0.5% to about 5%, by total weight, of a carboxylated polyurethane resin. To achieve the full advantage of the present invention, the styling gel comprises about 1% to about 4%, by total weight of the composition, of a carboxylated polyurethane resin.

The polyurethane resins are linear, hydroxyl-terminated copolymers having pendant carboxyl groups. The carboxyl group can be a carboxylic acid group or an ester group, wherein the alkyl moiety of the ester group contains one to three carbon atoms. The hydrophilic polyurethane resins typically are ethoxylated and/or propoxylated at least at one terminal end. The carboxylated polyurethane resin also can be a copolymer of polyvinylpyrrolidone and a polyurethane, having a CTFA designation PVP/polycarbamyl polyglycol ester. In accordance with an important feature of the present invention, the polyurethane resins can be solubilized in water, or in a hydroalcoholic solution, in the absence of a base.

The carboxylated polyurethane resins are soft and flexible, and have a melting point of about 40° C. to about 120° C., and preferably about 60° C. to about 100° C. To achieve the full advantage of the present invention, the polyurethane resins have a melting point of about 70° C. to about 90° C.

The carboxylated polyurethane resins provide treated hair with a conditioned, soft, nontacky, natural feel, while maintaining good style retention. The polyurethane resins also exhibit good wet combing and detangling properties, and are washable from the hair.

One useful polyurethane resin incorporated into a present hair styling gel comprises a reaction product of a diol component, an alkylene glycol, a diisocyanate, water, and a 2,2-di-(hydroxymethyl)-alkanoic acid. Alternatively, an amine, such as diglycolamine, can be substituted for at least a portion of the water in the reaction mixture. Aqueous solutions of the carboxylated polyurethane resins impart a soft feel, good set retention, reduced flaking and crust, and improved hair setting and conditioning properties to treated hair.

The hydrophilic polyurethanes are prepared using an aliphatic diisocyanate, an aromatic diisocyanate, or a mixture thereof. An aliphatic diisocyanate is preferred. Typically, the diisocyanate is interacted with a low molecular weight glycol or triol, such as ethylene glycol, diethylene glycol, propylene glycol, glycerol, hexylene glycol, cyclohexanediol, cyclohexanedimethanol, 1,4-butanediol, tripropylene glycol, triethylene glycol, dipropylene glycol, or mixtures thereof, wherein the glycol or triol has at least two hydroxyl groups and a molecular weight up to about 200, to provide a polyurethane. The diisocyanate also can be reacted with a polymeric dihydroxy-terminated oligomer, e.g., a polyoxyalkylene glycol having a molecular weight of about 200 to 20,000 to provide a hydrophilic polyurethane. Exemplary oligomers include, but are not limited to, polypropylene glycols, polyethylene glycols, ethylene glycol-propylene glycol copolymers, polybutylene glycols, and mixtures thereof. Preferably, a diisocyanate is interacted both with a low molecular weight diol or triol and with an oligomer to provide a hydrophilic polyurethane.

Exemplary, but nonlimiting, diisocyanates include trimethylhexamethylene diisocyanate, isophorone diisocyanate, decamethylene-1,10-diisocyanate, cyclohexane-1,2-diisocyanate, methylene bis(cyclohexyl-4-isocyanate), toluene-1,4-diisocyanate, toluene-2,6-diisocyanate, diphenylmethane-4,4'-diisocyanate, 3,3,'-dimethyldiphenylmethane-4,4'-diisocyanate, m-phenylene diisocyanate, p-phenylene diisocyanate, chlorophenylene diisocyanate, hexamethylene-1,6-diisocyanate, tetramethylene-1,4-diisocyanate, cyclohexane-1,4-diisocyanate, naphthalene-1,5-diisocyanate, 1-methoxyphenyl-2,4-diisocyanate, 4,4'-biphenylene diisocyanate, 3,3'-dimethoxy-4,4'-biphenyl diisocyanate, 3,3'-dimethyl-4,4'-biphenyl diisocyanate, 3,3'-dichlorophenyl-4,4'-diisocyanate, 2,2',5,5'-tetrachlorodiphenyl-4,4'-diisocyanate, trimethylhexamethylene diisocyanate, m-xylene diisocyanate, and mixtures thereof.

The polyurethane resin contains pendant carboxyl groups to improve the water solubility or dispersibility of the polyurethane resin. Preferably, the number of carboxyl groups is sufficient to give the polyurethane resin an acid value of at least about 7, and preferably about 7 to about 50, mg KOH/g resin. Examples of useful carboxylated polyurethanes are disclosed in Gould et al. U.S. Pat. No. 5,000,955, incorporated herein by reference. Other useful hydrophilic polyurethanes are disclosed in U.S. Pat. Nos. 3,822,238; 4,156,066; 4,156,067; 4,255,550; and 4,743,673, also incorporated herein by reference.

In one embodiment, the polyurethane resin comprises the reaction product of: a diol component comprising a polyoxyalkylene diol, preferably a polyoxyethylene diol having a number average molecular weight ($M_n$) of about 200 to about 20,000, a polyoxypropylene diol having an $M_n$ of about 200 to about 2500, a block copolymer of ethylene oxide and propylene oxide having an $M_n$ of about 1,000 to about 9,000, or a polyoxytetramethylene diol having an $M_n$ of about 200 to about 4,000; about 0.01% to about 10% by weight of a low molecular weight alkylene glycol selected from the group consisting of ethylene glycol, propylene glycol, 2-ethyl-1,3-hexanediol, tripropylene glycol, triethylene glycol, 2,4-pentanediol, 2-methyl-1,3-propanediol, 2-methyl-1,3-pentanediol, cyclohexanediol, cyclohexanedimethanol, dipropylene glycol, diethylene glycol, and mixtures thereof; an organic diisocyanate; a 2,2-di-(hydroxymethyl)alkanoic acid; and water in an amount of about 0.01% to about 0.45% by weight of the reaction mixture, wherein the NCO/OH ratio (i.e., the R-value) is about 0.5 to about 1, and preferably about 0.6 to about 0.98. To achieve the full advantage of the present invention, the R-value is about 0.65 to about 0.98.

An amine can be used in the reaction mixture for at least a portion of the water. The amine can be added to the reaction mixture in an amount of about 0.01% to about 0.8% by weight amine, preferably about 0.02% to about 0.5% amine to about 0.01% to about 0.2% water in the reaction mixture. Amines that can be used in the reaction are ethylenediamine, propylenediamine, monoethanolamine, diglycolamine, and JEFFAMINE D1-230, D-400, D-2000, D-4000, ED-0600, ED-900, or ED-2001. The hydroxylamines and the JEFFAMINE products are manufactured by Texaco Chemical Company. Preferably, the amine is a hydroxylamine, and most preferably the amine is monoethanolamine and/or diglycolamine.

The polyoxyethylene diols are available from Union Carbide Corporation under the trademark CARBOWAX, such as CARBOWAX® 1450 and CARBOWAX® 8000 wherein the number represents number average molecular weight. The polyoxypropylene diols (PPG) are available from various sources, such as the PPG series of ARCO NIAX® PPG 1025, PPG 425, PPG 725, PPG 1225, and PPG 2025, and as R2134 (2200) and R2135 (4400), wherein the number represents number average molecular weight. Triols are also available from ARCO as NIAX® Polyols 11-34, LG-650, LG-56, LG-168, LHT-28, LHT-240. The polyoxytetramethylene diols are available from E. I. DuPont de Nemours as TERATHANE 600, 1000, 1400, 2000, and 2900. Polyetherpolycarbonate is available from BASF under the tradename polytetrahydrofuran 1000 CD and 2000 CD.

A block polyoxyalkylene polymer also can be used in the reaction. For example, a propylene oxide terminated block of ethylene glycol manufactured by BASF under the tradename PLURONIC R and a ethylene oxide terminated block of propylene glycol manufactured by BASF under the tradename of PLURONIC can be used for the polyoxyalkylene in the reaction. Examples of the block copolymers of the sequential addition of ethylene oxide and propylene oxide to ethylene diamine are made by BASF under the tradename of PLURONIC, such as PLURONIC F68, F64, F127, L35, L92, L82, 17R2, and 25R2.

Preferably, the polyoxyalkylene diol used in forming the hydrophilic polyurethane resin is polyoxyethylene diol. The blends of polyoxyalkylene diols contain at least about 10% polyoxyethylene diol, preferably, at least 20% polyoxyethylene diol, and most preferably, at least 25% polyoxyethylene diol, by weight.

The amount of polyoxyalkylene diol having a molecular weight of 400 to 20,000 in the polyurethane resin can vary from about 10% to about 90%, preferably about 30% to about 90%, and most preferably about 40% to about 90%, by weight, and the number average molecular weight ($M_n$) of the polyoxyalkylene diol can vary from about 200 to about 20,000, preferably from about 800 to about 15,000, and more preferably from about 1000 to about 12,000.

The alkylene glycols can be purchased from numerous sources. For example, propylene glycol can be purchased from Aldrich Chemical Company as 1,2-propanediol. The amount of the alkylene glycol (hard segment) component in the polyurethane resin can be about 0.01% to about 20%, preferably about 0.05% to about 15%, more preferably about 0.1% to about 12%, still more preferably about 0.5% to about 10%, and most preferably about 1% to about 8%, by weight of the reaction mixture.

The diisocyanate in the reaction mixture can be an aliphatic diisocyanate, an aromatic diisocyanate, or a mixture thereof. The aliphatic diisocyanates are preferred. An especially preferred diisocyanate is methylene bis(cyclohexyl-4-isocyanate). Other examples of diisocyanates are trimethyl hexamethylene diisocyanate and isophorone diisocyanate. Representative examples of the preferred aliphatic diisocyanates include, but are not limited to tetra-methylene diisocyanate, hexamethylene diisocyanate, trimethylene diisocyanate, trimethylhexamethylene diisocyanate, cyclohexane-1,2-diisocyanate, and cyclohexane-1,4-diisocyanate. Examples of aromatic diisocyanates are 2,4- toluene diisocyanate and 2,6-toluene diisocyanate. Also suitable are the isocyanate equivalents which form urethane linkages, exemplified by nitrile carbonates, such as adiponitrile carbonate of U.S. Pat. No. 4,810,543, incorporated herein by reference. The amount of diisocyanate varies from about 3% to about 80%, preferably from about 4% to about 70%, more preferably from about 5% to about 60%, still more preferably from about 6% to about 55%, and most preferably from about 6.5% to about 50%, by weight. The polyurethane resins are prepared by reacting the polyoxyalkene diols with the diisocyanates.

The amount of water in the reaction mixture is about 0.03% to about 0.40%, and more preferably about 0.05% to about 0.35%, by weight, of the reaction mixture.

The amount of 2,2-di-(hydroxymethyl)alkanoic acid in the reaction mixture is about 0.1% to about 8%, preferably about 0.3% to about 7%, and most preferably about 0.5% to about 6%, by weight. Preferably the 2,2-di-(hydroxymethyl)alkanoic acid is dimethylolpropionic acid. The final reaction product has an acid value of at least about 0.2, preferably at least about 0.5, and most preferably at least about 1.

The ratio of NCO to OH groups from the diol, alkylene glycol, amines and water (i.e., the R-value) in the reaction mixture is about 0.5 to about 1, preferably about 0.6 to about 0.98, and most preferably from about 0.65 to about 0.98. The weight average molecular weight ($M_w$) of the carboxylated polyurethane resin is about 15,000 to about 300,000, preferably about 30,000 to about 200,000, and most preferably about 40,000 to about 190,000. The sum of all ingredients, including the diols, glycols, water, and diisocyanate in the reaction mixture total 100% by weight.

In another embodiment, the hydrophilic polyurethane resin comprises a reaction product of: (a) a diol having a major portion of a polyoxyethylene diol having an $M_n$ of 6,000 to 10,000, and a minor portion of a polyoxypropylene diol having an $M_n$ of about 1,000 to about 3,500 or a polyoxyethylene diol having an $M_n$ of about 600 to about 2000; (b) an alkylene glycol; (c) a diisocyanate; (d) water in an amount of about 0.01% to about 0.45% by weight of the reaction mixture; and (e) a 2,2-di(hydroxymethyl)alkanoic acid, and an equivalent mole weight ratio of NCO to OH of the water, diol and glycol of about 0.6 to about 0.98. Preferably, at least 45% of the polyoxyethylene glycol of $M_n$ about 8000, more preferably at least about 55%, still more preferably at least about 65%, and most preferably at least 75%, by weight, is used in the total reaction mixture. The amount of the lower molecular weight polyoxyethylene diol having an $M_n$ of about 600 to about 2,000 is about 1% to about 15%, and preferably from about 2% to about 10%, by weight of the reaction mixture. Preferably, the alkylene glycol is diethylene glycol, cyclohexanedimethanol, dipropylene glycol, or a mixture thereof.

The 2,2-di-(hydroxymethyl)alkanoic acid preferably is dimethylolpropionic acid. The amount of dimethylolpropionic acid is about 0.1% to about 8%, preferably about 0.3% to about 7%, and most preferably about 0.5% to about 6% by weight of the reaction mixture. The final product has an acid value of at least about 7 mg KOH/g resin. To achieve the full advantage of the invention, the polyurethane resin has an acid value of about 7 to about 50 mg KOH/g resin. The sum of all ingredients, including the diols, glycols, water, and diisocyanate in the reaction mixture totals 100% by weight.

Alternatively, an amine can be used in place of a portion of the water in the reaction mixture. An amount of about 0.15% to about 0.6% amine, based on diglycolamine, is used with about 0.06% to about 0.5% of water, more preferably about 0.1% to about 0.4% of water, and most preferably of about 0.15% to about 0.3% of water.

The preferred diol is a polyoxyethylene diol, preferably a polyoxyethylene diol of $M_n$ about 6000 to about 10,000, alternatively with about 1% to about 10% of a polyoxyethylene diol of $M_n$ about 600 to about 2,000. The preferred water level is about 0.03% to about 0.4%, and most preferably about 0.05% to about 0.35%, by weight.

The carboxylated polyurethane resins of this embodiment are especially useful in hair setting compositions because the polyurethane resins are soluble in ethanol/water mixtures, and in dilute neutral to basic aqueous solutions. The polyurethane resins also impart improved feel and conditioning to treated hair, low flaking and crust, and improved set retention. These and other advantageous properties are observed when the carboxylated polyurethane resins are admixed with an optional second hair fixative resin, e.g., increased water solubility of the second hair fixative resin, improved feel of treated hair, and reduced crust and flaking.

For hair setting compositions, the hydrophilicity of the polyurethane resin is an unexpected important property in combination with other desirable properties, such as washability. Conventional hair fixative resins are hydrophobic materials that impart a stiff feel to treated hair. The polyurethane resins are hydrophilic materials that give hair a soft, natural feel, yet are adhesive to the hair and impart excellent hair set retention. A combination of a conventional hair fixative resin and a polyurethane resin retains the desirable properties of each resin, and allows a desired degree of stiffness to be imparted to the hair. It also has been found that the hair styling properties of the polyurethane resin can be effected by small changes in the amount of water, the ratio of NCO/OH, and the amount of the di(hydroxymethyl)alkanoic acid in the reaction mixture.

The weight average molecular weight of the carboxylated polyurethane resins can be adjusted by modifying the amount of water in the reaction mixture within a predetermined range. The above-described polyurethane resins having an $M_w$ of about 30,000 to about 75,000, and preferably about 35,000 to about 50,000; and a kinematic viscosity at 3 wt. % in 55/42 ethanol/water (by weight) of about 4 to about 40 centistokes (cs), are formed using about 0.1% to about 0.3% by weight water in the reaction mixture, an NCO/OH ratio (i.e., R-value) of about 0.75 to about 0.95, and about 0.5% to about 2.7% by weight of the reaction mixture of dimethylolpropionic acid.

A polyurethane resin having an $M_w$ of about 55,000 to about 300,000 can be formed using about 0.3% to about 0.45% by weight water, a preferred NCO/OH ratio of about 0.75 to about 0.98, and about 0.5% to about 2.7% by weight dimethylolpropionic acid.

Polyurethane resins prepared using about 0.08% to about 0.45% by weight water in the reaction mixture, and an NCO/OH ratio of about 0.55 to about 0.95, preferably from about 0.6 to about 0.7, have a set retention at 30 minutes of about 80% to about 90%. An amount of water of about 0.15% to about 0.45% by weight in the reaction mixture and an NCO/OH ratio of about 0.6 to about 0.92, preferably from about 0.7 to about 0.9, can be used to provide polyurethane resins having a set retention of about 85% to about 98% at 30 minutes.

Alternatively, small amounts of diglycolamine can be substituted for the water in the reaction mixture, e.g., about 0.02% to about 1%, preferably from about 0.03% to about 0.75%, more preferably from about 0.04% to about 0.5%, and most preferably from 0.05% to about 0.4% by weight diglycolamine can be used in the reaction mixture.

The alkylene glycol used in this embodiment can be, for example, ethylene glycol, diethylene glycol, propylene glycol, dipropylene glycol, cyclohexanediol, 1,4-butanediol, cyclohexanedimethanol, tripropylene glycol, or triethylene glycol; preferably diethylene glycol, cyclohexanedimethanol, or dipropylene glycol; and most preferably diethylene glycol. The amount of the alkylene glycol (hard segments) in the reaction mixture is about 0.01% to about 20%, preferably about 0.05% to about 15%, more preferably about 0.1% to about 12%, still more preferably about 0.5% to about 10%, and most preferably about 1% to about 5%, by weight.

In each embodiment, the polyurethane-forming reaction is catalyzed by known catalysts. Tin-containing catalysts, such as tin salts or organotin esters, for example, stannous octoate and dibutyltin dilaurate, or tertiary amines, such as triethylene diamine and N,N,N',N'-tetramethyl-1,3-butane diamine, are preferred. The catalyst is used in an amount effective to catalyze the reaction, i.e., about 0.001 to 1 weight percent of the total weight of the reactive components. Reaction temperature is about 40° C. to about 120° C.

In the previous embodiments, the carboxylated polyurethane resin contained carboxylic acid groups. However, carboxylated polyurethane resins wherein carboxylic acid groups are converted to ester groups with an alcohol having one to three carbon atoms also can be utilized as the carboxylated polyurethane resin.

Other useful carboxylated polyurethane resins are PVP/polycarbamyl polyglycol esters, which are copolymers of polyvinylpyrrolidone and polyurethane. These carboxylated polyurethane resins are available commercially from Phoenix Chemical, Inc., Somerville, N.J., as PECOGEL A-12, PECOGEL H-12, PECOGEL H-115, and PECOGEL H-1220.

In addition to the carboxylated polyurethane resin, the hair styling gel contains 0% to about 6%, and preferably about 0.25% to about 5%, by weight of an optional second hair fixative resin. To achieve the full advantage of the present invention, the hair styling gel contains about 0.5% to about 4%, by weight of the composition of the second hair fixative resin. Preferably, the weight ratio of optional second hair fixative resin to carboxylated polyurethane resin in the composition is about one or less, i.e., 0 to about 1. The second hair fixative resin can be a nonionic, cationic, or anionic resin, because the carboxylated polyurethane resin is compatible with each class of resins. It also is envisioned that the optional second hair fixative resin is a mixture of two or more hair fixative resins in a total amount of 0% to about 6% by weight of the composition.

The second hair fixative resin preferably is a hydrophobic compound that retards the tendency of hair to absorb water. The second hair fixative resin also is a hard, brittle compound having a glass transition temperature of about 100° C. or greater, e.g., up to 200° C., and preferably about 110° C. or greater. An important feature of the second hair fixative resin is to reduce flaking attributed to the carboxylated polyurethane resins, and to impart to the hair the properties typically associated with the second hair fixative resin, e.g., stiffness.

In particular, the optional second hair fixative resin can impart a desired and predetermined degree of stiffness to the hair. In contrast, the carboxylated polyurethane resin provides an elastic, flexible film on the hair, which gives the hair a soft, natural feel. However, consumers often equate a good hair setting composition with a degree of hair stiffness. The present hair styling gels, therefore, impart the desired stiffness to the hair, while further providing the benefits attributed to the polyurethane resin, such as conditioning, good style retention, and good hair feel.

Nonlimiting examples of second hair fixative resins useful in the present hair spray compositions can be found in Grollier et al. U.S. Pat. No. 4,445,521, incorporated herein by reference. Specific second hair fixative resins include, but are not limited to, acrylamide copolymers, acrylamide/sodium acrylate copolymer, acrylate/ammonium methacrylate copolymer, acrylate copolymers, acrylic/acrylate copolymers, adipic acid/dimethylaminohydroxypropyl diethylenetriamine copolymer, adipic acid/epoxypropyl diethylenetriamine copolymer, allyl stearate/VA copolymer, aminoethylacrylate phosphate/acrylate copolymer, ammonium acrylate copolymers, ammonium vinyl acetate/acrylate copolymers, AMP acrylate/diacetoneacrylamide copolymers, AMPD acrylate/diacetoneacrylamide copolymers, butyl ester of ethylene/maleic anhydride copolymer, butyl ester of PVM/MA copolymer, calcium/sodium PVM/MA copolymer, corn starch/acrylamide/sodium acrylate copolymer, diethylene glycolamine/epichlorohydrin/piperazine copolymer, dodecanedioic acid/cetearyl alcohol/glycol copolymer, ethyl ester of PVM/MA copolymer, isopropyl ester of PVM/MA copolymer, karaya gum, methacryloyl ethyl betaine/methacrylate copolymers, octylacrylamide/acrylate/butylaminoethyl methacrylate copolymers, octylacrylamide/acrylate copolymers, phthalic anhydride/glycerin/glycidyl decanoate copolymer, phthalic/trimellitic/glycol copolymers, polyacrylamide, polyacrylamidomethylpropane sulfonic acid, polybutylene terephthalate, polyethylacrylate, polyethylene, polyquaternium-1, polyquaternium-2, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyvinyl acetate, polyvinyl butyral, polyvinyl imidazolinium acetate, polyvinyl methyl ether, PVM/MA copolymer, PVP, PVP/dimethylaminoethylmethacrylate copolymer, PVP/eicosene copolymer, PVP/ethyl methacrylate/methacrylic acid copolymer, PVP/hexadecene copolymer, PVP/VA copolymer, PVP/vinyl acetate/itaconic acid copolymer, shellac, sodium acrylate/vinyl alcohol copolymer, sodium carrageenan, starch diethylaminoethyl ether, stearylvinyl ether/maleic anhydride copolymer, sucrose benzoate/sucrose acetate isobutyrate/butyl benzyl phthalate copolymer, sucrose benzoate/sucrose acetate isobutyrate/butyl benzyl phthalate/methyl methacrylate copolymer, sucrose benzoate/sucrose acetate isobutyrate copolymer, vinyl acetate/crotonate copolymers, vinyl acetate/crotonic acid copolymer, vinyl acetate/crotonic acid/methacryloxybenzophenone-1 copolymer, vinyl acetate/crotonic acid/vinyl neodecanoate copolymer, and mixtures thereof.

In addition to the carboxylated polyurethane resin and the optional second hair fixative resin, the hair styling gel contains about 0.01% to about 3%, and preferably about 0.1% to about 2%, by weight of the composition, of a viscosity enhancer. To achieve the full advantage of the present invention, the hair styling gel contains about 0.2% to about 1.5%, by weight, of a viscosity enhancer. The viscosity enhancer can be a gelling agent, a thickener, or any other compound capable of providing a flowable semisolid composition having a viscosity of about 10,000 to about 100,000 cps.

The viscosity of a present hair styling gel comprising a carboxylated polyurethane resin and an optional second hair fixative resin in water is about 10,000 to about 100,000, and preferably about 20,000 to about 1000,000, cps. The achieve the full advantage of the present invention, the hair styling gel has a viscosity of about 30,000 to about 90,000 cps (as measured on a Brookfield Viscometer with a #6 spindle at 5 rpm).

The identity of the viscosity enhancer, therefore, is not limited, as long as the viscosity enhancer is compatible with the carboxylated polyurethane resin, and, if present, the second hair fixative resin, and does not adversely affect the stability or efficacy of the hair styling gel. Nonlimiting exam- ples of viscosity enhancers include, but are not limited to, acacia, acrylate/steareth-20 methacrylate copolymer, agar, algin, alginic acid, ammonium acrylate copolymers, ammonium alginate, amylopectin, attapulgite, bentonite, $C_{9-15}$ alcohols, calcium alginate, calcium carrageenan, capramide DEA, carbomers, carboxymethyl hydroxyethylcellulose, carboxymethyl hydroxypropyl guar, carrageenan, cellulose, cellulose gum, cocamide DEA, cocamide MEA, cocamide MIPA, cocoyl sarcosinamide DEA, corn starch, damar, dextrin, dibenzylidene sorbitol, ethylene dihydrogenated tallowamide, ethylene dioleamide, ethylene distearamide, gelatin, guar gum, guar hydroxypropyltrimonium chloride, hectorite, hyaluronic acid, magnesium silicates, methoxy PEG-22/dodecyl glycol copolymer, methylcellulose, microcrystalline cellulose, montmorillonite, myristamide DEA, myristamide MEA, myristamide MIPA, oat flour, oleamide DEA, oleamide MEA, oleamide MIPA, palmamide DEA, palmamide MEA, palmamide MIPA, palmitamide DEA, palmitamide MEA, palm kernelamide DEA, palm kernelamide MEA, palm kernelamide MIPA, peanutamide MEA, peanutamide MIPA, pectin, PEG-2M, PEG-5M, PEG-7M, PEG-9M, PEG-14M, PEG-20M, PEG-23M, PEG-45M, PEG-90M, PEG-115M, polyacrylic acid, polyvinyl alcohol, potassium alginate, potassium aluminum polyacrylate, potassium carrageenan, potato starch, propylene glycol alginate, ricinoleamide DEA, ricinoleamide MEA, ricinoleamide MIPA, sodium acrylate/vinyl alcohol copolymer, sodium carboxymethyl dextran, sodium carrageenan, sodium cellulose sulfate, sodium lauroyl sarcosinate, sodium myristoyl sarcosinate, sodium oleate, sodium palmitate, sodium polymethacrylate, sodium polystyrene sulfonate, sodium silicoaluminate, sodium stearate, sodium sulfate, sodium tallowate, soyamide DEA, stearalkonium bentonite, stearalkonium hectorite, stearamide DEA, stearamide MEA, stearamide MIPA, tallamide DEA, tallowamide DEA, tallowamide MEA, TEA-hydrochloride, tragacanth gum, tromethamine magnesium aluminum silicate, undecylenamide DEA, undecylenamide MEA, wheat flour, wheat starch, xanthan gum, hydrated silica, hydroxybutyl methylcellulose, hydroxyethylcellulose, hydroxyethyl ethylcellulose, hydroxyethyl stearamide-MIPA, hydroxypropylcellulose, hydroxypropyl guar, hydroxypropyl methylcellulose, hydroxystearamide MEA, isostearamide DEA, isostearamide MEA, isostearamide MIPA, karaya gum, kelp, lanolinamide DEA, lauramide DEA, lauramide NEA, lauramide MIPA, lecithinamide DEA, linoleamide DEA, linoleamide MEA, linoleamide MIPA, locust bean gum, magnesium aluminum silicate, and mixtures thereof.

The hair styling gel also can contain 0% to about 20%, by total weight of the composition, of a lower alcohol, i.e., an alcohol having one to seven carbon atoms. Preferably, the composition contains 0% to about 15%, by weight, of a lower alcohol. In order to reduce the adverse environmental affects attributed to volatile organic compounds, the amount of alcohol is maintained at as low a level as possible without adversely affecting the esthetics or efficacy of the hair styling gel. To achieve the full advantage of the present invention, the composition is free of a lower alcohol.

The alcohol typically used in the hair spray composition is ethanol, although isopropyl alcohol also can be incorporated into the composition. The carboxylated polyurethane resins are readily solubilized in water and in a wide range of hydroalcoholic solutions, without the addition of a basic neutralizer, thereby permitting a decrease in the amount of alcohol present in the hair styling gel.

The hair styling gel also contains water as the predominant carrier. The amount of water is maximized in order to minimize the amount of VOC in the composition and to maximize composition viscosity. Because the carboxylated polyurethane resins are hydrophilic, it is not necessary to include a base in the water to neutralize and solubilize the polyurethane resin. The carboxylated polyurethane resin also assists in solubilizing the optional second hair fixative resin.

Other optional ingredients also can be incorporated into the hair styling gel. The identity of the optional ingredients is not limited as long as the optional ingredients do not adversely affect the esthetics or efficacy of the hair styling gel. Such optional ingredients are well known to those skilled in the art, e.g., emulsifiers such as anionic or nonionic surfactants; preservatives such as benzyl alcohol, methyl paraben, propyl paraben, or imidazolidinylurea; cationic conditioners such as cetyl trimethyl ammonium chloride, stearyl dimethyl benzyl ammonium chloride, and di(partially hydrogenated tallow) dimethyl ammonium chloride; coloring agents such as any of the FD&C or D&C dyes; perfume oils; and chelating agents such as ethylenediaminetetraacetic acid. These optional ingredients generally are included individually at a level of 0% to about 5%, by weight of the total composition.

The aqueous formulations of the present invention also can contain conventional hair care adjuvants in amounts which generally range from 0% to about 2% by weight, and preferably 0% to about 1% by weight. Among the additives which can be used are plasticizers such as glycols, phthalate esters, and glycerine, silicones, emollients, lubricants, and penetrants such as various lanolin compounds, protein hydrolysates and other protein derivatives, ethylene adducts and polyoxyethylene cholesterol.

The hair styling gels of the present invention are prepared by simply admixing and dissolving the polyurethane resin and the optional second hair fixative resin in an aqueous or hydroalcoholic carrier, with heating if necessary. Then, an aqueous solution of the viscosity enhancer and any optional ingredients is admixed with the aqueous solution of the hair setting resins to provide a homogeneous hair styling gel.

EXAMPLE A

Preparation of a Carboxylated Polyurethane Resin A

A polyoxyethylene diol having an $M_n$ of 8000 was heated under vacuum to 0.048% of water, then 744 parts of the dried diol was added to 21 parts diethylene glycol, 4.3 parts dimethylolpropionic acid, and 0.37 parts water. The resulting mixture was heated, with stirring, until a homogenous melt was obtained. Then, 88 parts methylene bis-cyclohexyl-4-4'-diisocyanate was added to the mixture. The NCO/OH ratio was about 0.98. When the temperature reached about 65° C., 2.25 ml of dibutyl tin dilaurate was added to the mixture, and the mass exothermed. The mass then was heated to 100° C., and held at 100° C. for about one hour to complete polyurethane formation. The polyurethane resin had a weight average molecular weight ($M_w$) of 141,000. At 5% concentration, the polyurethane resin dissolved in 55/45 ethanol water to give a solution having a viscosity of 180 cps. At a concentration of 3%, in 60/40 propylene glycol/water, the solution had a viscosity of 5300 cps. A gel containing 19% of the polyurethane resin in 20/80 propylene glycol/water was tough, exceptionally clear and adhered to glass. The viscosity of the gel was reduced by raising the pH to about 7.0.

EXAMPLE B

Preparation of Polyurethane Resin B

A polyoxyethylene diol having an $M_n$ of 8000 was heated under vacuum to 0.037% of water, then 744 parts of the dried diol was added to 21 parts diethylene glycol, 18.6 parts dimethylolpropionic acid, and 0.23 parts water. The resulting mixture was heated, with stirring, until a homogenous melt was obtained. Then, 115 parts methylene bis-cyclohexyl-4,4'-diisocyanate was added to the mixture. The NCO/OH ratio was about 0.98. When the temperature reached about 65° C., 2.25 ml dibutyl tin dilaurate was added to the mixture, and the mass exothermed. The mass then was heated to 100° C., and held at 100° C. for about one hour to complete polyurethane formation. The polyurethane resin had an $M_w$ of 63,000. At 5% concentration, the polyurethane resin dissolved in 55/45 ethanol water to give a solution having a viscosity of 1680 cps, and a reduced viscosity of 225 cps upon the addition of 2 ml ammonia to 180 grams of the solution. At a concentration of 3%, in 60/40 propylene glycol/water, the solution had a viscosity of 144 cps. A gel containing 19% of polymer in 20/80 propylene glycol/water was tough, exceptionally clear, and adhered to glass, displaying improved adhesive properties compared to gels made using a polyurethane without the alkanoic acid.

EXAMPLE C

Preparation of a Carboxylated Polyurethane Resin C

Polyoxyethylene diol having an $M_n$ of 8000 was heated under vacuum to 0.060% of water, and 736 parts of the dried diol was added to 21 parts of diethylene glycol, 18 parts of dimethylolpropionic acid, and 0.96 part of water. The mixture was heated with stirring until a homogeneous melt was obtained. Then, 114 parts of methylene bis-cyclohexyl-4-4'-diisocyanate were added. The NCO/OH ratio was 0.85. When the temperature reached about 63° C., 1.85 ml of dibutyltin dilaurate was added, and the mass was allowed to exotherm. The mass was heated at 100° C. for about one hour to complete formation of the polyurethane resin. The polyurethane resin dissolved in slightly basic 55/45 ethanol/water solution (wt/wt) at a concentration of 5 wt. % was clear and had a viscosity of 14 cps. The polyurethane resin had an $M_w$ of 40,000 and was used in a hair styling aid to give a superior soft feel, excellent set retention, low crust, and low flaking properties to treated hair. The hair styling aid imparted a crust rating of 4.9, a feel of 6.7, a flaking rating of 7, a set retention of 97% at 30 minutes, and a set retention of 95% at 60 minutes to treated hair.

EXAMPLE D

Preparation of Polyurethane Resin D

Polyoxyethylene diol having an $M_n$ of 8000 was heated under vacuum to 0.215% of water, and 736 parts of the dried diol was added to 21 parts of diethylene glycol, 59 parts of dimethylolpropionic acid, and 1.81 parts of water. The mixture was heated with stirring until a homogeneous melt was obtained. Then, 168 parts of methylene bis-cyclohexyl-4-4'-diisocyanate were added. The NCO/OH ratio was 0.65. When the temperature reached about 7° C., 1.85 ml of dibutyltin dilaurate was added, and the mass was allowed to exotherm. The mass was heated at 100° C. for about one hour to complete formation of the polyurethane resin. The polyurethane resin had an $M_w$ of 15,000 and dissolved in slightly basic 55/45 ethanol/water (wt/wt) solution at a concentration of 5 wt. % was clear and had a viscosity of 10 cps. The polyurethane resin had a kinematic viscosity of 4.60 cps in 55/42/3 ethanol/water/polymer solution by weight. The polyurethane resin was used in a hair styling aid to impart superior soft feel, excellent set retention, low crust, and low flaking properties to treated hair. The hair styling aid imparted a crust rating of 4.5, a feel of 4.5, a flaking rating of 1.8, and a set retention of 85% at 30 minutes to treated hair.

An important property of a hair styling gel is the ability to wash the hair setting resin from the hair, and thereby avoid polymer build-up on the hair. In accordance with an important feature of the present invention, the carboxylated polyurethane resin used in the hair styling gel can be removed from the hair by simply shampooing the hair. The unexpected washability of the hair spray composition is attributed to the hydrophilic nature of the polyurethane resin, and especially to the acid value of the carboxylated polyurethane resin. When the acid value of the hydrophilic polyurethane resin is at least about 7 mg KOH/g of resin, the polyurethane resin can be rinsed from the hair during shampooing without the need to neutralize the resin with an organic base.

The acid value is an indication of the number pendant carboxylic acid groups on the polyurethane resin backbone. Although noncarboxylated polyurethane resins are hydrophilic, they are difficult to wash from the hair in a short time. Washability is enhanced by incorporating pendant carboxylic acid groups onto the polyurethane backbone.

The effect of acid value is illustrated in Table 1, wherein it is shown that washability is independent of $M_w$ or R-value, but varies with acid value. In effect, carboxylated polyurethane resins having an acid value of about 7 mg KOH/g resin or greater, i.e., about 7 to about 50 mg KOH/g resin, had improved washability over resins having an acid value less than 7 mg KOH/g resin.

TABLE 1

PROPERTIES OF POLYURETHANE RESINS (R-VALUE = 0.73 TO 0.98)

| Polyurethane Resin | R-value | Water | Acid Value[1] | Molecular Weight[2] | PDI[3] | Washability[4] |
|---|---|---|---|---|---|---|
| 1 | 0.98 | low | 0.42 | 174,000 | 2.00 | no |
| 2[5] | 0.98 | low | 2.28 | 141,000 | 2.00 | no |
| 3 | 0.84 | low | 8.01 | 28,000 | 2.00 | yes |
| 4[6] | 0.98 | low | 8.28 | 63,000 | 2.00 | yes |
| 5 | 0.98 | medium | 0.50 | 188,000 | 2.20 | no |
| 6 | 0.85 | medium | 2.47 | 64,000 | 1.90 | no |
| 7 | 0.88 | medium | 7.87 | 30,000 | 1.60 | yes |
| 8 | 0.90 | medium | 7.70 | 43,000 | 1.80 | yes |
| 9 | 0.90 | medium | 8.04 | 39,000 | 1.70 | yes |
| 10 | 0.94 | medium | 7.78 | 39,000 | 1.80 | yes |
| 11 | 0.90 | high | 7.70 | 46,000 | 1.90 | yes |

[1] The acid value was measured by titrating a solution of the resin with potassium hydroxide, the acid value is expressed in milligrams of KOH per gram of polyurethane;
[2] The molecular weight is the weight average molecular weight ($M_w$) measured by size exclusion chromatography using polyethylene glycol calibration standards;

TABLE 1-continued

PROPERTIES OF POLYURETHANE RESINS (R-VALUE = 0.73 TO 0.98)

| Polyurethane Resin | R-value | Water | Acid Value[1] | Molecular Weight[2] | PDI[3] | Washability[4] |
|---|---|---|---|---|---|---|

[3]PDI is an abbreviation for "polydispersity index," i.e., the ratio [Weight average molecular weight]/[Number average molecular weight], which measures the relative spread in the molecular weight of the polyurethane resin;

[4]The washability of the resin was determined by applying 3 wt. % solution of polyurethane resin onto clean, 2 gram, 6-inch long hair tresses, allowing the hair to dry, then washing the hair tresses with shampoo and warm water for about 3 minutes;

[5]Polyurethane Resin A; and

[6]Polyurethane Resin B.

To demonstrate the hair styling gels of the present invention, several styling gels were prepared. Each composition contained 0.5% to 2% by weight of a carboxylated polyurethane resin. The compositions of Examples 1–6 in Table 2 contained a polyurethane resin having an $M_w$ of about 40,000 and a nonionic viscosity enhancer. The compositions of Examples 7–13 in Table 3 contained a carboxylated polyurethane resin having an $M_w$ of about 15,000 and an anionic viscosity enhancer.

Each composition was prepared by dissolving the carboxylated polyurethane resin and the second hair fixative resin in a mixture of water and ethanol at 60° C. After cooling to room temperature, an aqueous solution of the viscosity enhancer was added to the resin solution, with mixing, until a homogeneous hair styling gel was provided.

TABLE 2

| Example | 1 | 2 | 3 | 4 | 5 | 6 |
|---|---|---|---|---|---|---|
| D.I. Water | 38.10[7] | 37.85 | 38.25 | 37.75 | 38.05 | 38.05 |
| Ethanol | 10.00 | 10.00 | 10.00 | 10.00 | 10.00 | 10.00 |
| Polyurethane Resin C[8] | 0.75 | 0.75 | 0.75 | 0.75 | 0.75 | 0.50 |
| D.I. Water | 50.00 | 50.00 | 50.00 | 50.00 | 50.00 | 50.00 |
| METHOCEL 40-100[9] | 0.75 | 1.00 | | | | |
| VERSENE 100[10] | 0.40 | 0.40 | | | | |
| NATROSOL 250[11] | | | 1.00 | 1.50 | 1.00 | 1.00 |
| Citric Acid (50%) | | | | | 0.20 | 0.20 |
| PVP K-120[12] | | | | | | 0.25 |
| Total | 100.00 | 100.00 | 100.00 | 100.00 | 100.00 | 100.00 |
| Gel Appearance | clear | clear | clear | clear | clear | clear |
| Viscosity | viscous fluid | viscous fluid | viscous fluid | elastic, viscous fluid | elastic, viscous fluid | elastic, viscous fluid |

[7]percent by weight of the composition;
[8]a carboxylated polyurethane resin having a molecular weight of about 40,000, as set forth in Example C;
[9]METHOCEL 40-100 is a poly(hydroxypropyl methylcellulose) available commercially from Dow Chemical Co., Midland, MI;
[10]VERSENE-100 is tetrasodium EDTA, an ion chelating agent available commercially from Dow Chemical Co.;
[11]NATROSOL-250 is a hydroxyethyl cellulose polymer available commercially from Aqualon Co., Wilmington, DE; and
[12]PVP K-120 is polyvinylpyrrolidone with K-value = 120, as defined in "Kollidon" by Wolker Buhler, BASF, Ludwigshafen, Ch. 2, 2nd edition (1993).

TABLE 3

| Example | 7 | 8 | 9 | 10 | 11 | 12 | 13 |
|---|---|---|---|---|---|---|---|
| D.I. Water | 25.00[7] | 25.00 | 50.00 | 50.00 | 50.00 | 50.00 | 50.00 |
| Ethanol | 5.00 | 5.00 | | | | | |
| Polyurethane Resin D[13] | 2.00 | 2.00 | 2.00 | 2.00 | 2.00 | 2.00 | 2.00 |
| D.I. Water | 66.60 | 66.50 | 46.50 | 46.495 | 46.49 | 46.47 | 46.45 |
| Carhopol, Ultrez[14] | 0.40 | 0.50 | 0.50 | 0.50 | 0.50 | 0.50 | 0.50 |
| TEA (50%)[15] | 1.00 | 1.00 | 1.00 | 1.00 | 1.00 | 1.00 | 1.00 |
| Polyacrylamide | | | | 0.005 | 0.01 | 0.025 | 0.05 |
| Total | 100.00 | 100.00 | 100.00 | 100.00 | 100.00 | 100.00 | |
| Gel Appearance | sl. hazy | sl. hazy | sl. hazy | sl. hazy | sl. hazy | sl. hazy | sl. hazy |
| Viscosity | viscous | viscous | viscous | viscous | viscous | viscous | viscous |
| Tactile Property | | | | stringy | stringy | stringy | stringy |

[13]a carboxylated polyurethane resin having an $M_w$ of about 15,000, as set forth in Example D;
[14]a polyacrylic acid available from B. F. Goodrich Co., Cleveland, O; and
[15]triethanolamine, 50% in water.

Examples 1–13 in Tables 2 and 3 show that hair styling gels containing a carboxylated polyurethane resin and a viscosity enhancer, and having a low VOC (e.g., 10% by weight or less), can be prepared. Tables 2 and 3 further show that a hair styling gel containing a low molecular weight polyurethane resin (e.g., about 15,000) or a high molecular weight polyurethane resin (e.g., about 40,000) can be prepared.

The hair styling gels also impart good hold and hair set retention to treated hair. For example, a hair styling gel containing a carboxylated polyurethane resin having an $M_w$ of about 30,000 or greater provided equal or better set retention at 70% relative humidity than a control hair spray product containing the resin AMPHOMER. AMPHOMER is an acrylic copolymer resin and is widely used in commercial aerosol and pump hair spray products. Hair setting products containing AMPHOMER, therefore, were used as a control for comparison to hair setting compositions containing a polyurethane resin.

In tests designed to test the ability of a present hair styling gel to hold a hair set, hair styling gels containing 3 parts by weight carboxylated polyurethane resin and 0.5 parts by weight of a viscosity enhancer dissolved in a mixture of 10 parts by weight ethanol and 86.5 parts by weight water were prepared. The compositions were used in a test to determine the ability of the hair styling gel to maintain a hair set at 25° C. and 70% relative humidity over a 24-hour period.

The set retention test measures the ability of a hair styling gel to hold or retain a hairstyle for an extended time at a particular relative humidity. Set retention was measured by applying 0.5 cc (cubic centimeters) of the hair styling gel to a one gram hair tress, and testing six tresses per composition. The sprayed tresses were allowed to dry overnight, at 30% relative humidity (i.e., RH), in a zigzag shape. The tresses were hung inside a humidity chamber at 25° C. and a predetermined relative humidity (e.g., 70% RH). The relaxed length was recorded of the tresses and set retention was calculated using the equation:

$$\% \text{ Set Retention} = \frac{L - L_t}{L - L_o} \times 100,$$

wherein L is the length of the fully extended tress, $L_o$ is the length of treated hair before relaxation, $L_t$ is the length after of exposure for a time, t. Six tresses were tested per hair styling gel composition and the data was statistically analyzed and compared at the 95% confidence level. In all the experiments, AMPHOMER was used as the resin in a control hair setting product.

Hair set retention was measured at a low relative humidity (i.e., 70% RH) at 25° C. Table 4 summarizes hair set retention tests from hair styling gels incorporating carboxylated polyurethane resins of different $M_w$. The hair set retention results were compared to the results provided by a control hair styling gel containing AMPHOMER. The comparative tests show that hair styling gels containing a carboxylated polyurethane resin having an $M_w$ of about 30,000 or greater, e.g., about 30,000 to about 200,000, exhibited comparable or improved hair set retention over AMPHOMER. The hair set retention provided by the carboxylated polyurethane resins, therefore, is considered to be excellent because AMPHOMER is used in successful commercial hair setting compositions.

TABLE 4

HAIR SET RETENTION OF POLYURETHANE RESINS
25° C., 70% Relative Humidity

| Polyurethane Resin | Molecular Weight ($M_w$) | % Set Retention, 30 min. | % Set Retention, 1 hour | % Set Retention, 2 hours | % Set Retention, 24 hours |
| --- | --- | --- | --- | --- | --- |
| 5 | 188,000 | 95.7 | 93.5 | 92.2 | 89.7 |
| 1 | 174,000 | 94.6 | 91.1 | 90.5 | 87.4 |
| 2[5] | 141,000 | 95.0 | 90.8 | 90.0 | 84.7 |
| 6 | 64,000 | 90.2 | 83.5 | 81.3 | 75.4 |
| 46 | 63,000 | 91.5 | 86.7 | 83.6 | 81.3 |
| 11 | 46,000 | 90.0 | 86.3 | 83.5 | 76.2 |
| 8 | 43,000 | 88.1 | 83.2 | 79.8 | 67.71 |
| 9 | 39,000 | 92.3 | 86.1 | 78.9 | 69.86 |
| 10 | 39,000 | 88.3 | 82.94 | 78.22 | 67.80 |
| 7 | 30,000 | 81.63 | 66.5 | 59.4 | 50.0 |
| 3 | 28,000 | 77.9 | 71.23 | 68.38 | 60.05 |
| AMPHOMER[16] | not available | 84.6 | 76.1 | 71.8 | 63.1 |

[16]AMPHOMER is a commercial hair fixative resin available from National Starch and Chemical Corp., Bridgewater, NJ and is an octylacrylamide/acrylates/butylaminoethylmethacrylatecopolymer.

The following is another example of a hair styling gel of the present invention that was easily and uniformly applied to the hair, and exhibited good hair styling and hair set retention properties. The hair styling gel contains a hydrophilic copolymer of a polyurethane and polyvinylpyrrolidone. The hair styling gel is free of alcohol, and contains water as the sole component of the carrier.

| Ingredients | % wt. |
| --- | --- |
| Deionized water | 92.437 |
| Carbomer[17] | 0.403 |
| Ammonium hydroxide | 0.480 |
| PECOGEL H-12[18] | 6.680 |

[17]CARBOPOL 940, a polyacrylic acid available commercially from B. F. Goodrich Co., Brecksville, O; and
[18]PECOGEL H-12, a 12% by wt. copolymer of polyurethane and polyvinylpyrrolidone, distributed by Phoenix Chemicals Inc., Somerville, NJ.

Accordingly, a preferred hair styling gel contains a carboxylated polyurethane resin having a weight average molecular weight of about 30,000 to about 200,000. At a molecular weight below about 30,000, the carboxylated polyurethane resin has a reduced ability to hold the hair in a predetermined configuration for a sufficient time to meet consumer demands, unless a second optional hair fixative resin is present in the hair styling gel. If the molecular weight is greater than about 200,000, the hair styling gel can impart a tacky feeling to the hair. An optional second hair fixative resin also can be added to the hair styling gel to impart a desired degree of stiffness to treated hair.

A hair styling gel also possesses properties in addition to set retention in order to meet consumer demands. In particular, the present, consumer-acceptable hair styling gels impart a good feel to the hair and avoid excessive flaking and crust. Hair styling gels that provide natural, or reduced, crusts are desired. Hair crust is tested subjectively in this test wherein a group of trained judges evaluate hair tresses treated with a hair styling gel. The hair flaking test measures the amount of flakes or dust that form on the hair after combing hair that has been treated with the composition and dried. The present hair styling gels imparted a consumer acceptable feel to treated hair, and the crust and flaking was within acceptable limits.

Many modifications and variations of the invention as hereinbefore set forth can be made without departing from the spirit and scope thereof, and, therefore, only such limitations should be imposed as are indicated by the appended claims.

What is claimed is:

1. A method of treating hair to fix the hair in a desired hairstyle comprising:

(a) wetting the hair;
    (b) applying a hair styling gel composition to the hair, said hair styling gel composition comprising
        (i) about 0.25% to about 6% by weight of a carboxylated polyurethane resin;
        (ii) about 0.01% to about 3% by weight of a viscosity enhancer; and
        (iii) about 15% to about 99.5% by weight water, wherein the carboxylated polyurethane resin has a weight average molecular weight of about 15,000 to about 300,000; and
    (c) then drying the hair while styling the hair into the desired hairstyle.

2. The method of claim 1 wherein the hair styling gel composition further comprises 0% to about 6% by weight of a second hair fixative resin.

* * * * *